(12) United States Patent
Matusaitis et al.

(10) Patent No.: US 8,568,418 B2
(45) Date of Patent: Oct. 29, 2013

(54) APPARATUS FOR CONTROLLING POSITION OF ROTARY SURGICAL INSTRUMENT

(75) Inventors: Tomas Matusaitis, Chicago, IL (US); Vlad Bluvshtein, Plymouth, MN (US); Sean Corrigan, Chicago, IL (US); Lori Lucke, Rosemount, MN (US)

(73) Assignee: Gyrus Ent L.L.C., Bartlett, TN (US)

( * ) Notice: Subject to any disclaimer, the term of this patent is extended or adjusted under 35 U.S.C. 154(b) by 207 days.

(21) Appl. No.: 13/251,493

(22) Filed: Oct. 3, 2011

(65) Prior Publication Data
US 2013/0085498 A1    Apr. 4, 2013

(51) Int. Cl.
*A61B 17/00*    (2006.01)

(52) U.S. Cl.
USPC .............................. 606/80; 606/83; 606/180

(58) Field of Classification Search
USPC ................... 606/79–81, 83, 167–171
See application file for complete search history.

(56) References Cited

U.S. PATENT DOCUMENTS

| | | |
|---|---|---|
| 4,345,192 A | 8/1982 | Kohzai et al. |
| 4,646,738 A | 3/1987 | Trott |
| 5,030,900 A | 7/1991 | Kono et al. |
| 5,602,449 A | 2/1997 | Krause et al. |
| 5,669,921 A * | 9/1997 | Berman et al. ................ 606/167 |
| 5,672,945 A | 9/1997 | Krause |
| 5,707,350 A | 1/1998 | Krause et al. |
| 6,245,084 B1 | 6/2001 | Mark et al. |
| 7,247,161 B2 | 7/2007 | Johnston et al. |
| 7,318,831 B2 | 1/2008 | Alvarez et al. |
| 2010/0100112 A1 | 4/2010 | Kauker et al. |

FOREIGN PATENT DOCUMENTS

WO    WO 00/22994    4/2000

OTHER PUBLICATIONS

Mar. 1, 2013 International Search Report and Written Opinion issued in Application No. PCT/US2012/055069.

* cited by examiner

*Primary Examiner* — Andrew Yang
(74) *Attorney, Agent, or Firm* — Oliff & Berridge, PLC

(57) ABSTRACT

A rotation sensor system is included with a surgical instrument having an outer tube, an inner rotating member rotatably disposed within the outer tube and a handpiece coupled to proximal ends of the outer tube and the inner rotating member. The rotation sensor system includes a magnetic member provided on the inner rotating member near the proximal end of the inner rotating member, a magnetically permeable member provided on the outer tube near the proximal end of the outer tube, and a sensor provided on the handpiece to sense magnetic flux of the magnetically permeable member adjacent to the sensor. This sensed magnetic flux can be used to determine the rotational position of the inner rotating member relative to the outer. tube. Such information can be used to control the position of the cutting member relative to the cutting window when a surgeon stops rotating the inner rotating member.

14 Claims, 21 Drawing Sheets

APPARATUS FOR CONTROLLING POSITION OF ROTARY SURGICAL INSTRUMENT

BACKGROUND

This disclosure relates to surgical instruments, and in particular to surgical cutting instruments that use suction, for example, powered shavers, microdebriders and dissector blades.

Surgical apparatus used to shave, cut, resect, abrade and/or remove tissue, bone and/or other bodily materials are known. Such surgical apparatus can include a cutting surface, such as a rotating blade disposed on an elongated inner tube that is rotated within an elongated outer tube having a cutting window. The inner and outer tubes together form a surgical cutting instrument or unit. In general, the elongated outer tube includes a distal end defining an opening or cutting window disposed at a side of the distal end of the outer tube. The cutting window of the outer tube exposes the cutting surface of the inner tube (typically located at a side of the distal end of the inner tube) to tissue, bone and/or any other bodily materials to be removed. A powered handpiece is used to rotate the inner tube with respect to the outer tube while an outer tube hub (connected to the proximal end of the outer tube) is fixed to the handpiece and an inner tube hub (connected to the proximal end of the inner tube) is loosely held by the powered handpiece and is rotated by a motor of the handpiece.

In some instruments, the inner tube is hollow and has a cutting window on a side surface of its distal end such that tissue, bone, etc. will be cut or shaved as the cutting window of the inner tube aligns with and then becomes misaligned with the cutting window of the outer tube as the inner tube is rotated within the outer tube. In this regard, it can be said that the cutting device nibbles or takes away small pieces of the bone, tissue, etc. as the inner tube is rotated within the outer tube.

In some instruments, a vacuum is applied through the inner tube such that the bodily material that is to be cut, shaved, etc. is drawn into the windows of the inner and outer tubes when those windows become aligned, thereby facilitating the cutting, shaving, etc. of the tissue, which then travels through the inner tube due to the suction. It also is common to supply an irrigation fluid, which can include a liquid, to the surgical site via a passage provided between the inner and outer tubes.

Furthermore, such surgical instruments can be used during the surgical procedure to provide suction alone by stopping rotation of the inner tube and then aligning the windows of the inner and outer tube so that suction can be applied through those windows. At other times, it may be desirable to stop rotation of the inner tube so that the cutting window of the inner tube is misaligned with the cutting window of the outer tube, thereby blocking the outer tube cutting window, for example, so that tissue will not be drawn into those windows by the suction, which could irritate the tissue which is not intended to be removed. However, it can be difficult and/or time consuming for the surgeon to stop the inner tube at the desired orientation so that the windows either are aligned or are misaligned.

In particular, when the surgeon releases the activation switch which causes the motor to stop rotating the inner blade, the inner blade will stop in a random location without regard for whether or not the two windows are aligned (providing an open suction path and exposed cutting teeth), are partially aligned (partially open suction path and exposed cutting teeth) or are fully closed (fully closed suction path and guarded cutting teeth). Currently, after the surgeon releases the activation switch and the inner tube stops rotating, the surgeon views the position of the inner tube cutting window relative to the outer tube cutting window via an endoscope that also is disposed within the operation site. The surgeon then must intermittently tap the activation switch of the inner tube rotation motor to cause incremental rotation of the inner tube until the inner and outer cutting windows are in the desired relative position. This process causes fatigue and frustration in the surgeon, and also increases the time required to perform the surgical procedure.

Furthermore, it can be difficult to remotely sense the orientation of the inner cutting window relative to the outer cutting window particularly when the outer cutting tube having the outer cutting window can be positioned at various rotational orientations relative to the handpiece of the surgical instrument. For example, when the outer tube includes a bend, a surgeon often will adjust the orientation by which the outer tube is coupled to the handpiece so that the bend (and thus also the direction in which the outer cutting window faces) is appropriately adjusted for the surgical procedure. Thus, simply providing a sensor on the outer cutting tube can be technically complex because such a sensor would include wires that would need to move when the surgeon adjusts the rotational orientation of the outer tube relative to the handpiece.

SUMMARY

In accordance with at least some aspects of the invention, a rotation sensor system is provided for a surgical instrument having an outer tube, an inner rotating member that is rotatably disposed within the outer tube and a handpiece coupled to proximal ends of the outer tube and the inner rotating member. The rotation sensor system includes a magnetic member provided on the inner rotating member near the proximal end of the inner rotating member, a magnetically permeable member provided on the outer tube near the proximal end of the outer tube, and a sensor provided on the handpiece to sense magnetic flux of the magnetically permeable member adjacent to the sensor. As the inner rotating member rotates, the magnetic member on the inner rotating member will move relative to the magnetically permeable member on the outer tube. This will cause the magnetic flux generated by the magnetically permeable member to fluctuate as the inner rotating member rotates. The sensor detects fluctuation in the magnetic flux generated by the magnetically permeable member. This sensed magnetic flux can be used to determine the rotational position of the inner rotating member relative to the outer tube. Because (i) the position of a cutting member of the inner rotating member relative to the magnetic member is fixed and (ii) the position of a cutting window of the outer tube relative to the magnetically permeable member on the outer tube is fixed, the position of the cutting member of the inner rotating member relative to the cutting window of the outer tube can be determined from the sensor output. Such information can be used to control the position of the cutting member relative to the cutting window when the surgeon stops rotating the inner rotating member.

In accordance with some embodiments, the handpiece includes a longitudinal axis, and the magnetic member, the magnetically permeable member and the sensor are radially aligned with each other with respect to the longitudinal axis such that the magnetic member is disposed radially inward of the magnetically permeable member, and the magnetically permeable member is disposed radially inward of the sensor.

In accordance with one preferred embodiment, the magnetic member includes two oppositely polarized magnets disposed at diametrically opposite positions relative to a longitudinal axis of the inner rotating member. The two magnets are disposed such that a polarity of an outwardly-facing pole of a first one of the magnets is opposite to a polarity of an outwardly-facing pole of a second one of the magnets. In addition, the magnetically permeable member preferably includes two semicircular pieces of ferromagnetic material located on opposite circumferential segments near the proximal end of the outer tube. Opposing ends of the two semicircular pieces of ferromagnetic material are separated from each other by gaps. Thus, as the inner rotating member rotates within the outer tube, due to rotation of the two oppositely polarized magnets on the inner rotating member, the magnetic flux generated by the magnetically permeable members are opposite to each other at any given instant, but fluctuate (in polarity) as the inner rotating member rotates through 180°.

In accordance with some embodiments, the sensor is a dual axis linear magnetic sensor that senses magnetic flux in two perpendicular directions. Accordingly, the sensor will sense the magnetic flux in the portion of the semicircular piece or pieces of ferromagnetic material located adjacent to the sensor, and will output a signal that fluctuates as the magnetic flux generated from the semicircular piece(s) of ferromagnetic material fluctuate(s) during rotation of the inner rotating member.

Preferably, the surgical instrument also includes a controller that receives the sensor signal output from the sensor and determines a position of the cutting member relative to the cutting window based on the sensor signal. Upon receipt of a stop command from a user of the surgical instrument, the controller stops rotation of the inner rotating member and optionally positions the cutting member of the inner rotating member at a predetermined stop position relative to the cutting window of the outer tube. According to some embodiments, the controller allows the inner rotating member to stop at any random position, and then upon receipt of a command, slowly rotates the inner rotating member while monitoring the sensor output until the sensor output indicates that the predetermined stop position has been reached. According to other embodiments, the controller causes the inner rotating member to stop at the predetermined stop position automatically whenever a command is received to stop rotation of the inner rotating member. This can be accomplished, for example, by slowly rotating the inner rotating member upon receipt of a stop command while monitoring the sensor output until the sensor output indicates that the predetermined stop position has been reached.

According to preferred embodiments, the surgical instrument includes a coupling between the handpiece and the proximal end of the outer tube such that the outer tube can be attached to the handpiece at a variety of different rotational orientations. This allows the surgeon to vary the direction in which the cutting window of the outer tube faces. The coupling includes a first part on the handpiece and a second part on the proximal end of the outer tube. The first and second parts are adjustably attachable to each other at different selectable rotational orientations relative to the longitudinal axis of the handpiece, thereby permitting adjustment of the rotational orientation of the outer tube cutting window relative to the handpiece.

According to some embodiments, the inner rotating member is an inner hollow tube and the cutting member is a cutting window disposed near the distal end of the inner tube. With such embodiments, suction is applied through the inner tube, and that suction can be applied to the patient through the outer cutting window of the outer tube when the cutting windows of the inner and outer tubes are aligned with each other. Thus, the surgical instrument can be used for suctioning the surgical site even when a cutting operation is not being performed (that is, when the inner tube is not being rotated).

BRIEF DESCRIPTION OF THE DRAWINGS

Various exemplary embodiments of the disclosed surgical instrument will be described in detail with reference to the following drawings in which.

DETAILED DESCRIPTION OF EMBODIMENTS

The following exemplary embodiments are described below with reference to the figures in the context of human surgery, such as ear, nose and throat surgery, and in particular sinus surgery as well as head and neck surgery. The following exemplary embodiments may also be utilized in spinal surgery, orthopedic surgery, and various other surgical applications. All exemplary embodiments of the invention are intended to be used in any applicable field of endeavor.

Figure 1:
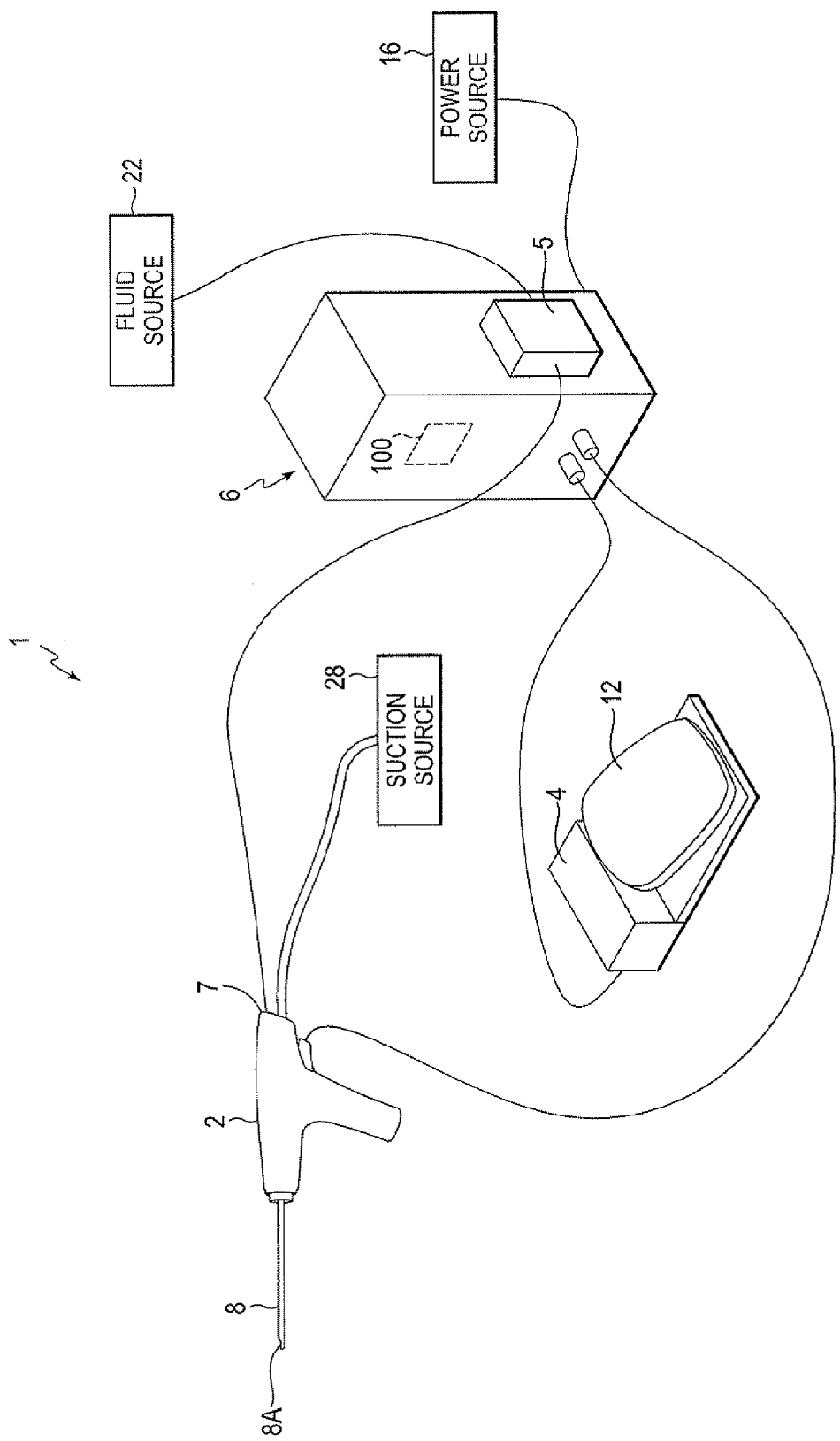
FIG. 1 illustrates a perspective view of a powered surgical instrument system that incorporates a surgical instrument, control unit, fluid source and suction source.

FIG. 1 is a schematic of a powered surgical instrument system. Except for the rotation sensor system, to be described hereafter, the system may be in accordance with the system described in U.S. Pat. No. 7,247,161, the disclosure of which is incorporated herein by reference in its entirety. Another system to which the invention is applicable is described in U.S. Pat. No. 7,318,831, the disclosure of which is incorporated herein by reference in its entirety. As shown in FIG. 1, the powered surgical instrument system 1 includes a handle (or handpiece) 2, a footswitch 4 (with pedal 12), fluid (liquid and/or gas) source 22, suction source 28, a control unit 6, fluid pump 5 and a fluid inlet/irrigation outlet 7. The system is supplied with power from a power source 16 such as a wall outlet. The suction source 28 may be an external suction source such as provided by attachment to a facility suction outlet provided on a wall. The handpiece 2 is connected, at its distal end, to a surgical instrument 8. The surgical instrument 8 in this embodiment includes a cutting tip at its distal end 8A that is used, for example, to cut, shave, remove, resect and/or abrade tissue, bone and/or other bodily materials.

Figure 2:
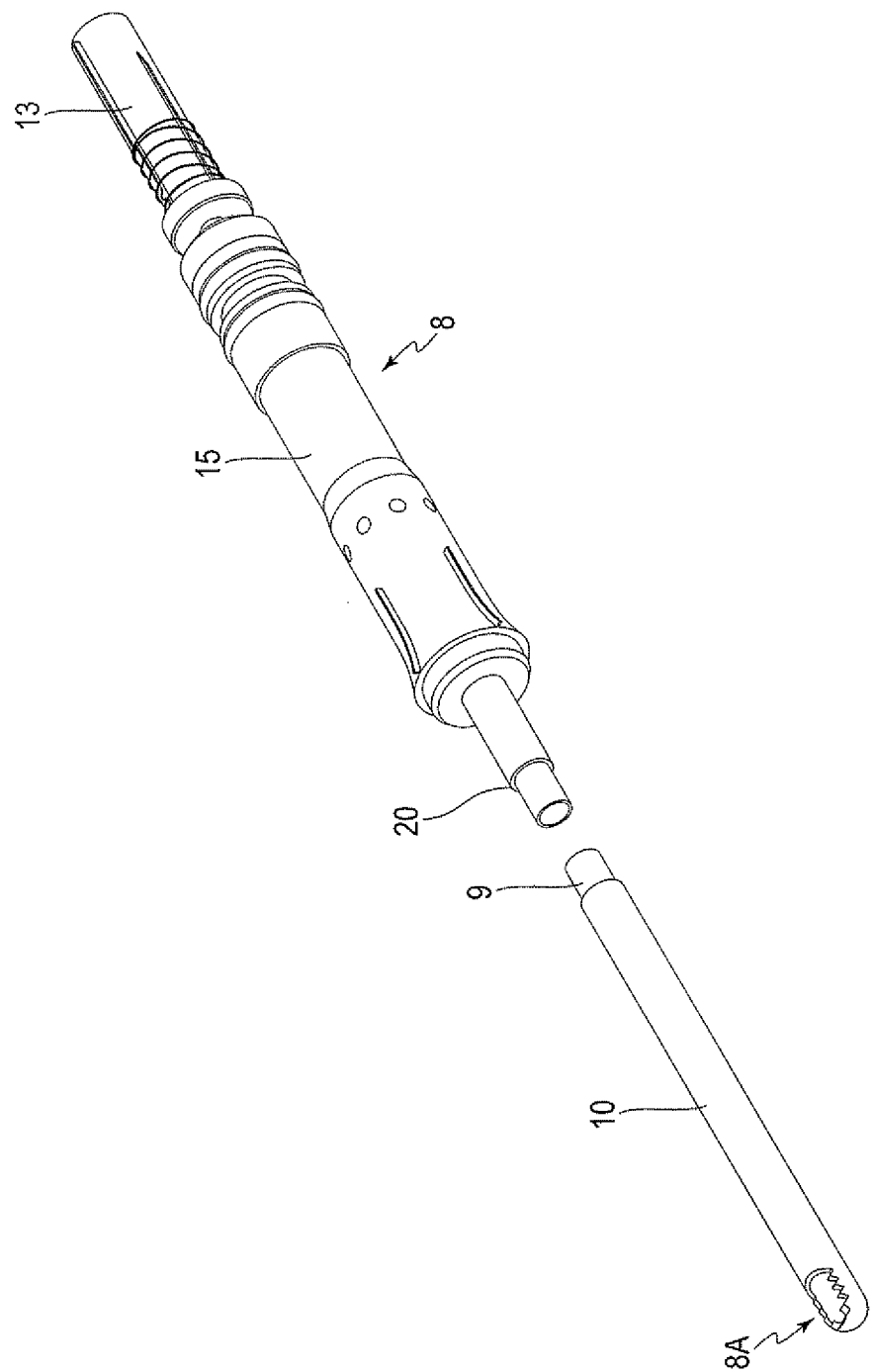
FIG. 2 is a perspective view of an exemplary embodiment of a surgical instrument in accordance with the present disclosure.

FIG. 2 illustrates a perspective view of an exemplary embodiment of the surgical instrument 8 in accordance with aspects of the invention. The instrument 8 incorporates an inner tube 9 and an outer tube 10. In this exemplary embodiment, an inner tube hub 13 is formed on the second end 14 (see FIG. 3) of the inner tube 9 and an outer tube hub 15 is formed on the second end 17 (see FIG. 3) of the outer tube 10. For purposes of this disclosure, each tube 9/10 and its hub 13/15 are collectively referred to as a "tube" or "member." The inner tube 9 is inserted into a fluid passage 20 formed within the outer tube 10 so that the inner tube 9 is co-axially disposed within the outer tube 10 until the external distal tip of the inner tube 9 contacts the internal distal surface of the outer tube 10. The outer tube 10 has a larger diameter than the inner tube 9, thus allowing for insertion of the inner tube 9 within the outer tube 10. However, it should be appreciated that the inner and outer tubes will be pre-assembled prior to delivery to the customer. Thus, a customer will most likely not be inserting the inner tube into the outer tube. Irrigation liquid can be supplied to the surgical site by supplying the liquid to the passage 20 via an inlet 26.

The inner and outer tube hubs 13, 15 couple the inner and outer tubes 9, 10, respectively, to the handpiece 2. Once coupled to the handpiece 2, the outer tube 10 will be fixed relative to the handpiece 2, but the inner tube 9 will be rotatable relative to the outer tube 10 and the handpiece 2.

Figure 3:
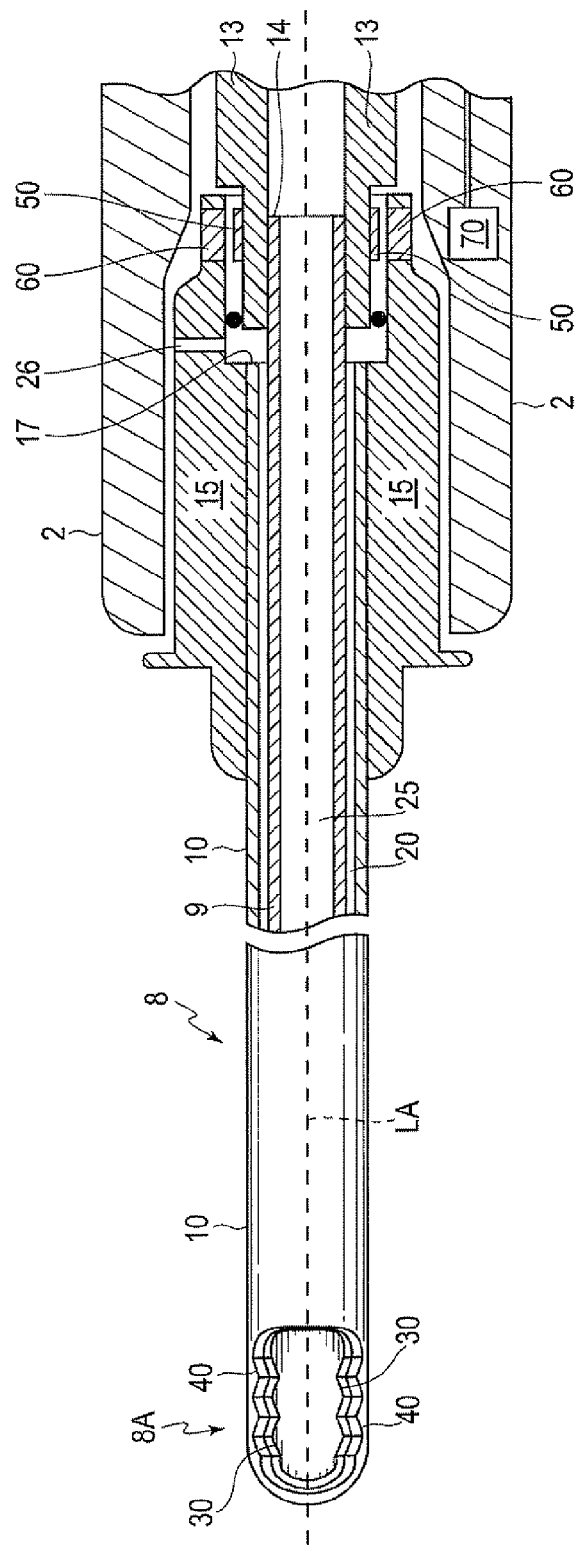
FIG. 3 is a side view, partially in perspective and partially in cross-section, of a surgical instrument having a rotation sensor system in accordance with an embodiment of the present disclosure.
Figure 4:
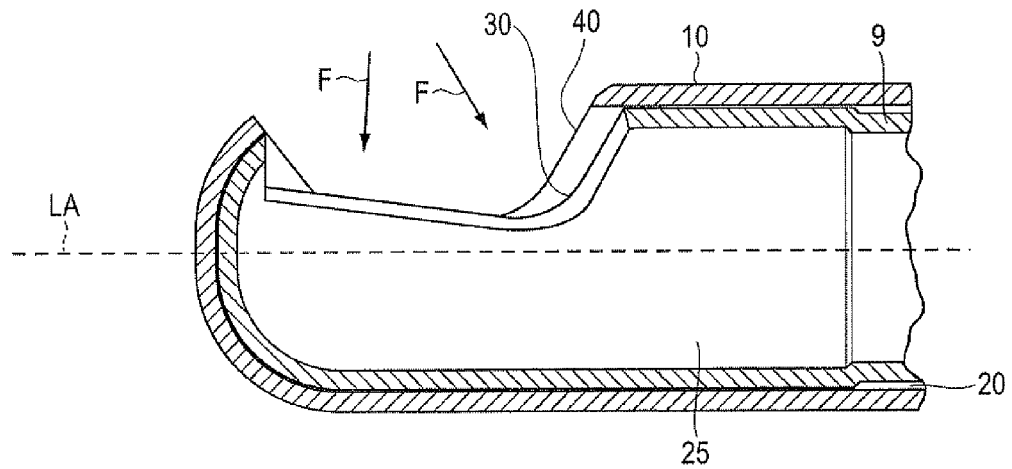
FIG. 4 is a side, cross-sectional view of the FIG. 3 surgical instrument distal tip with the cutting windows being in complete alignment.
Figure 5:
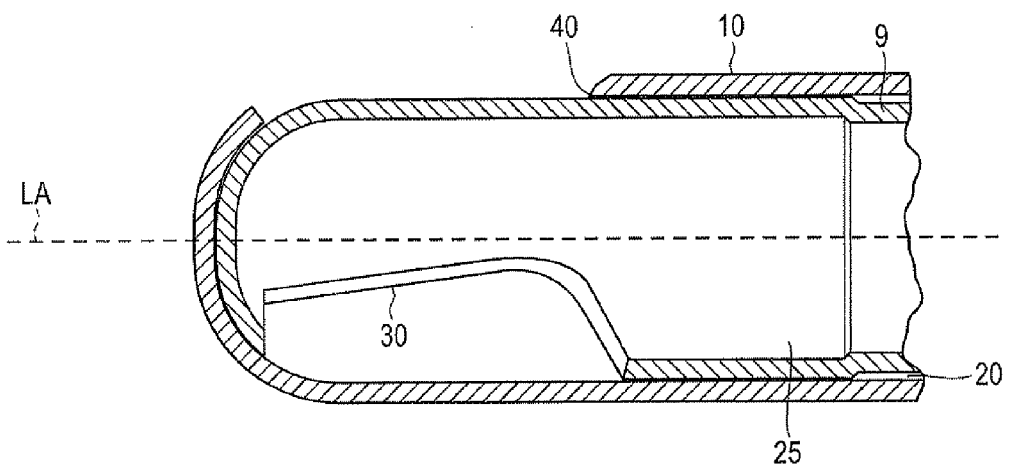
FIG. 5 is a side, cross-sectional view similar to FIG. 4, but with the cutting windows being in complete mis-alignment so that suction is not applied through the cutting windows.

Referring to FIG. 3, which shows a perspective view of the tip 8a and a cross-sectional view of the handpiece 2 and proximal ends of the cutting blades 9 and 10, the outer tube 10 includes a cutting window 40 disposed at a side of its distal end. Thus, the outer tube 10 can be referred to as a first cutting blade. The inner tube 9 also includes a cutting window 30 disposed at a side of its distal end. Thus, the inner tube 9 can be referred to as a second cutting blade. The edges of the cutting windows 30 and 40 can be serrated, smooth or a combination of serrated and smooth to form cutting surfaces. As mentioned previously, the inner cutting blade 9 rotates within the outer cutting blade 10, and thus as the inner cutting blade 9 rotates, the cutting windows 30 and 40 become aligned with each other as shown in FIG. 4 and then become misaligned with each other as shown in FIG. 5. When the cutting windows 30 and 40 are misaligned with each other as shown in FIG. 5, the side of the inner tube 9 distal tip opposite from the cutting window 30 blocks the cutting window 40 of the outer cutting blade 10.

The first, or outer cutting blade 10 thus is an outer tube having a proximal end and a distal end, with a cutting window 40 disposed at a side of the first cutting blade 10 near the distal end.

The inner, second cutting blade 9 is a tubular body having a proximal end and a distal end, with cutting window 30 disposed at a side of its distal end. As mentioned previously, the second, inner cutting blade 9 is rotatably disposed inside of the first, outer cutting blade 10 such that the surgical instrument 8 cuts tissue by rotating the second, inner cutting blade 9 within the first, outer cutting blade 10 while a vacuum is applied through an internal bore 25 of the cutting blade 9 to draw the tissue into the cutting windows 30 and 40 of the cutting blades 9 and 10 and sever the tissue by rotation of the cutting blade 9. Thus, the cutting blade 9 is an inner rotating member having a cutting member near its distal end. The inner rotating member need not be a tube. For example, the inner rotating member could be a shaft with a cutting member at its distal end. With such an arrangement, suction would be applied through the hollow outer tube 10.

FIG. 3 also shows the rotation sensor system in accordance with an embodiment of the invention. In order to detect the rotational position of inner cutting blade 9 relative to outer cutting blade 10, a rotation sensor system is provided. The rotation sensor system includes a magnetic member 50 provided on the inner cutting blade 9 near the proximal end of the inner cutting blade 9 (on hub 13), a magnetically permeable member 60 provided on the outer cutting blade 10 near the proximal end of the outer cutting blade (on hub 15), and a sensor 70 provided on the handpiece 2. The sensor 70 senses the magnetic flux of the magnetically permeable member 60 adjacent to the sensor 70. The output of the sensor 70 is provided to a controller 100, which is part of the control unit 6, and includes, for example, a microprocessor (CPU), working memory (RAM) and storage (ROM) in which appropriate programs for using the output of sensor 70 are stored.

Figure 6A:
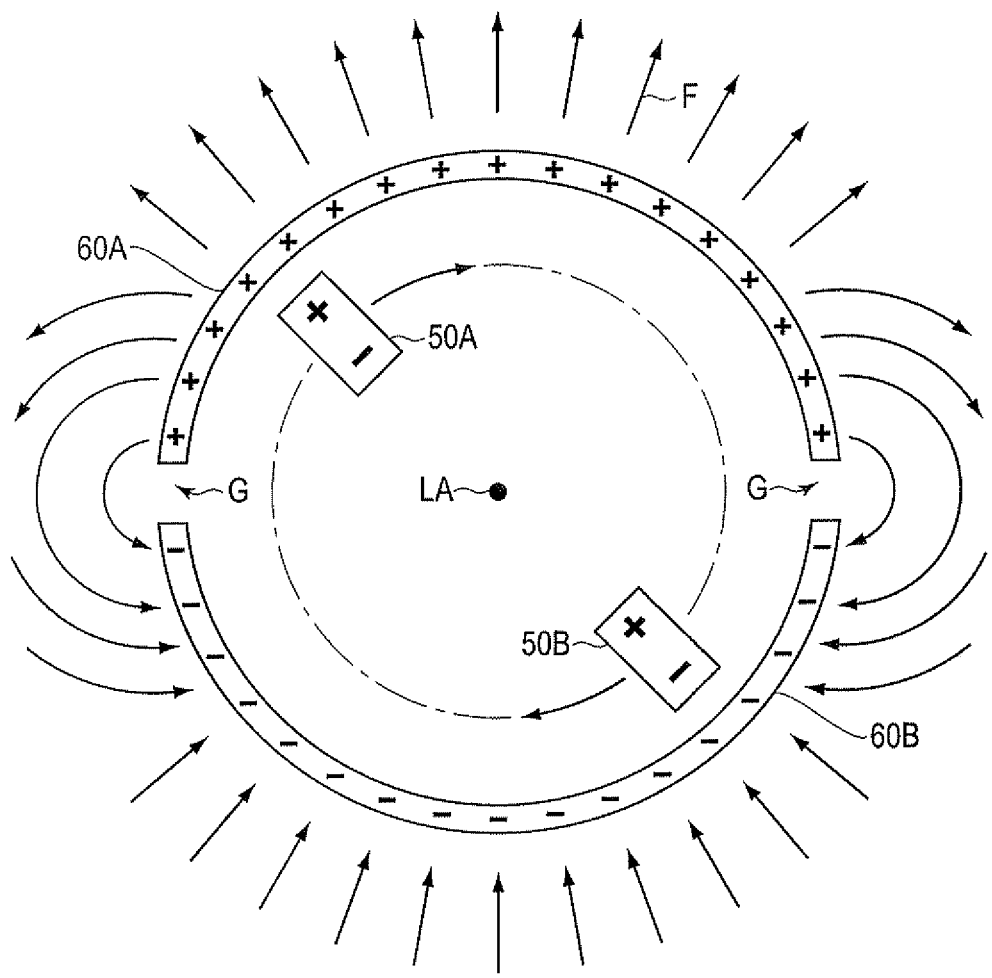
FIG. 6A is a cross-sectional view showing the magnetic members of an inner cutting blade and the magnetically permeable pieces of ferromagnetic material of the outer cutting blade.
Figure 6B:
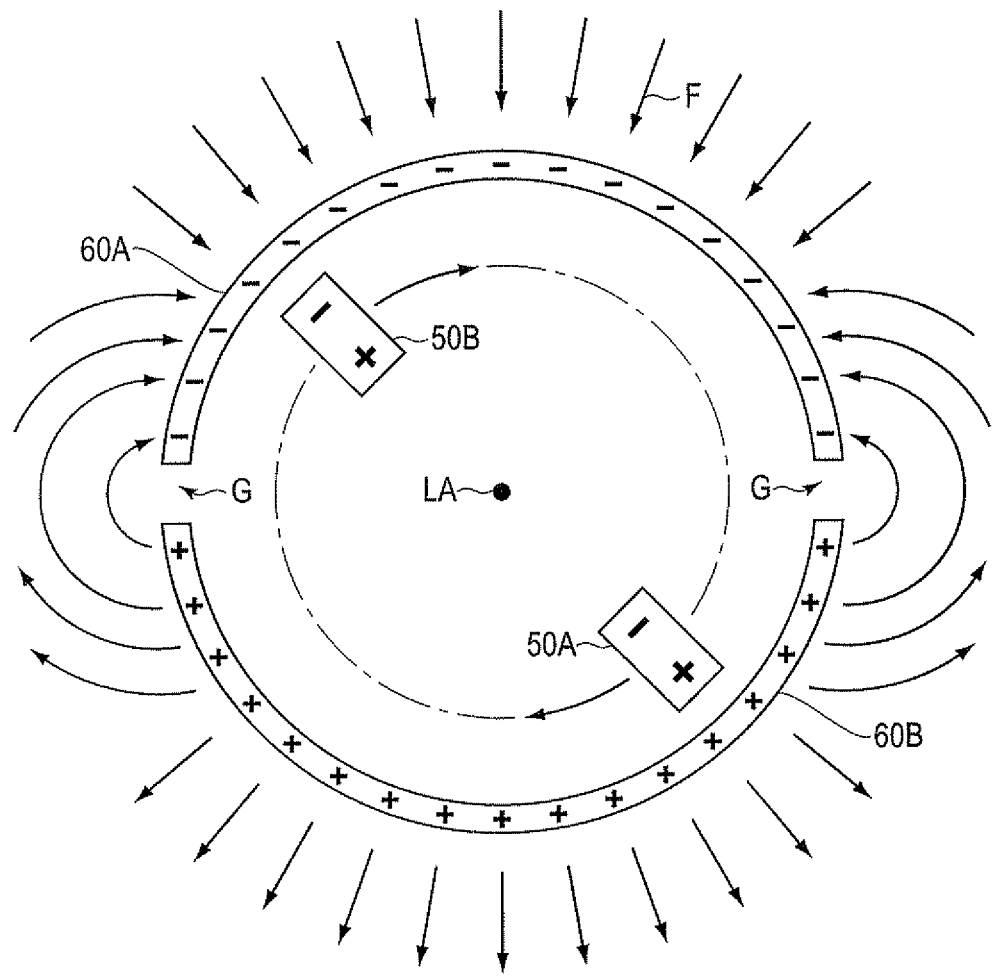
FIG. 6B is a view similar to FIG. 6A except that the inner cutting blade has rotated by 180° such that the direction of the magnetic flux induced in the magnetically permeable pieces has reversed.

The manner in which one embodiment functions will be described in conjunction with FIGS. 3, 6A and 6B. The handpiece 2 includes a longitudinal axis LA. As shown in FIG. 3, the magnetic member 50, the magnetically permeable member 60 and the sensor 70 are radially aligned with each other with respect to the longitudinal axis of the handpiece 2. In particular, the magnetic member 50 is disposed radially inward of the magnetically permeable member 60. (That is, magnetic member 50 is closer to the longitudinal axis LA than is the magnetically permeable member 60.) In addition, the magnetically permeable member 60 is disposed radially inward of the sensor 70. As shown in FIGS. 6A and 6B, the magnetic member 50 includes two oppositely polarized magnets 50a and 50b disposed at diametrically opposite positions relative to the longitudinal axis LA of the inner cutting blade 9, which also corresponds to the longitudinal axis LA of the handpiece 2. The magnets 50a and 50b are positioned such that a polarity of an outwardly-facing pole of a first one of the magnets (50a) is opposite to a polarity of an outwardly-facing pole of a second one of the magnets (50b). If the symbol + signifies the North pole and the symbol − signifies the South pole, as shown in FIGS. 6A and 6B, magnet 50a is arranged with its North pole facing radially outward, whereas magnet 50b is arranged with its South pole facing radially outward.

The magnetically permeable member 70 includes two semicircular pieces 60a and 60b of magnetically permeable material such as a ferromagnetic material (for example, NiFe). The two semicircular pieces 60a and 60b are located on opposite circumferential segments near the proximal end of the hub 15 associated with the outer cutting blade 10. Each of the pieces 60a and 60b extends almost one-half around the circumference of the hub 15. Opposing ends of the two semicircular pieces of ferromagnetic material 60a, 60b are separated from each other by gaps G as shown in FIGS. 6A and 6B. Magnetic flux will be induced in the ferromagnetic pieces 60a and 60b based on the polarity of the magnet surface (of magnets 50a and 50b) that is located adjacent to each particular ferromagnetic piece. When the inner cutting blade 9 is positioned with its magnets 50a and 50b as shown in FIG. 6A, magnetically permeable material piece 60a will have the same magnetic polarity as the outer face of magnet 50a, whereas magnetically permeable piece 60b will have the same magnetic polarity as the outer face of magnet 50b. When the inner cutting blade 9 has rotated by 180°, as shown in FIG. 6B, the polarities of the magnetically permeable material pieces 60a and 60b will be the opposite of that shown in FIG. 6A. Thus, as the inner cutting blade 9 rotates relative to the outer cutting blade 10, the polarities of the magnetically permeable material pieces 60a and 60b will fluctuate (instantaneously switch) between the states shown in FIGS. 6A and 6B, with their polarities switching each time the magnets 50a and 50b pass by the gaps G. Accordingly, the sensor 70 disposed adjacent to a portion of the magnetically permeable material 60 will sense the magnetic flux of the magnetically permeable material adjacent thereto, and thus will output a signal that fluctuates as the inner cutting blade 9 rotates.

Figure 7:
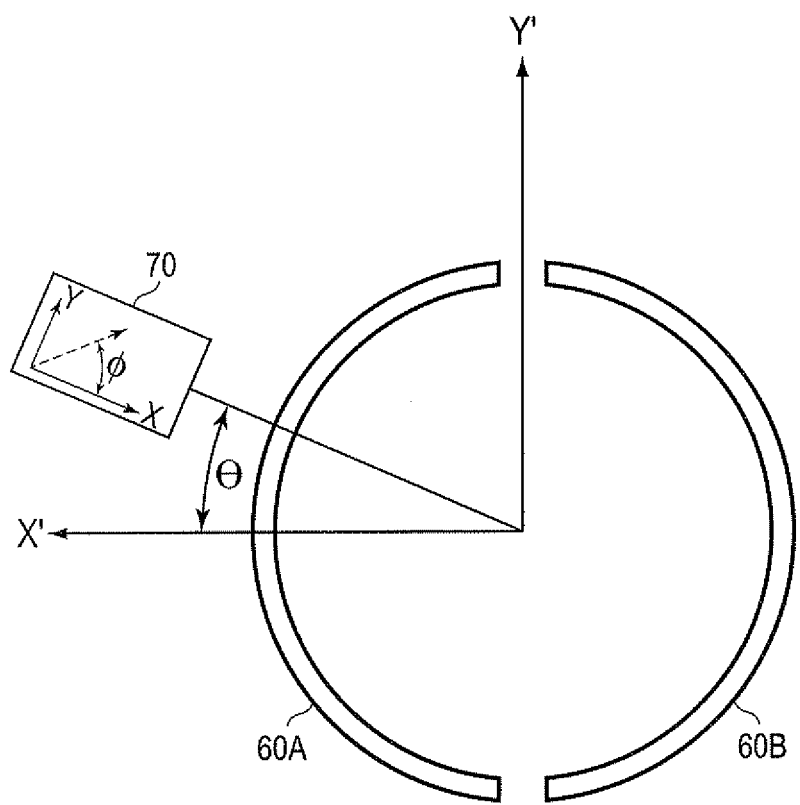
FIG. 7 shows a dual axis linear magnetic sensor positioned relative to the magnetically permeable member of the outer cutting blade.

FIG. 7 shows one example of sensor 70. According to a preferred embodiment, sensor 70 is a dual axis linear magnetic sensor that senses magnetic flux in two perpendicular directions (the X direction and the Y direction). The sensor 70 is positioned relative to the magnetically permeable material pieces 60a and 60b such that one of its measurement axes (the X axis shown in FIG. 7) is normal to the adjacent surface of the magnetically permeable structure.

It has been determined that, as long as the sensor 70 is positioned radially close enough to the magnetically permeable pieces 60a and/or 60b, the sensor 70 can effectively sense the instantaneous switching of the polarities of the magnetically permeable material located adjacent to the sensor regardless of where the sensor is located around the circumference of the magnetically permeable member defined by the magnetically permeable material pieces 60a and 60b. Accordingly, the disclosed arrangement is very effective at detecting the position of the inner cutting blade 9 relative to the outer cutting blade 10 even if the rotational orientation of the outer cutting blade 10 relative to the handpiece 2 (and thus relative to the sensor 70) is changed.

Figure 8A:
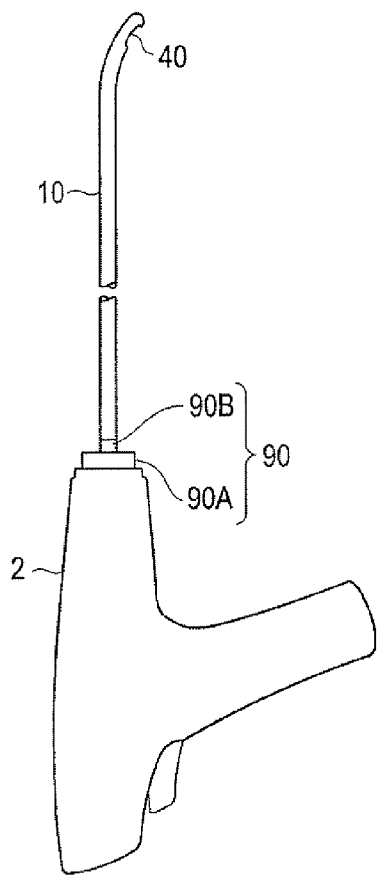
FIGS. 8A, 8B and 8C are side views of a surgical instrument showing the outer cutting blade positioned at three different positions relative to the handpiece.
Figure 8B:
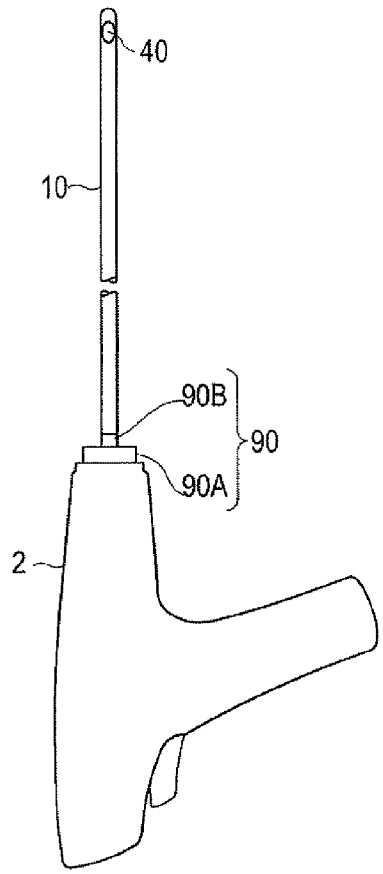
Figure 8C:
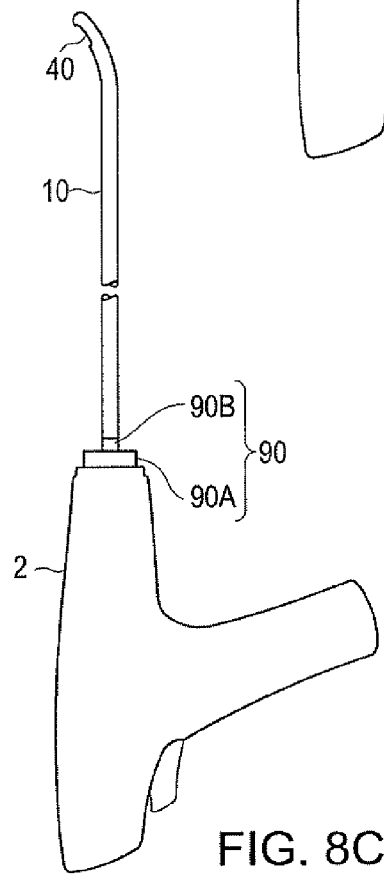

For example, FIGS. 8A-8C show a surgical instrument having an outer cutting blade 10 attached to handpiece 2 at three different positions. The cutting blade 10 is the same in each of FIGS. 8A, 8B and 8C; however, the orientation of the cutting blade 10 relative to the handpiece 2 differs in each of FIGS. 8A, 8B and 8C. As shown in FIG. 8A, the cutting blade 10 has a curved distal end with its cutting window 40 located on a radially inner portion of the curve. In FIG. 8A, the curve is to the right in the plane of the page. In FIG. 8B, the curve is out of the page, and in FIG. 8C, the curve is to the left within the plane of the page. A surgeon may wish to use the surgical instrument in one or more of these different orientations, as well as in other orientations. Accordingly, a coupling 90 is provided between the outer cutting blade 10 and the handpiece 2 such that the rotational orientation of the outer cutting blade 10 relative to the handpiece 2 can be varied. The coupling 90 includes a first part 90a on the handpiece 2 and a second part 90b on the outer cutting blade 10. The first and second parts 90a and 90b are adjustably attachable to each other at different selectable rotational orientations relative to the longitudinal axis LA of the handpiece so that a rotational orientation of the cutting window 40 of the outer cutting tube 10 can be varied relative to the handpiece 2. When the rotational orientation of the outer cutting tube 10 is changed, for example, from the orientation shown in FIG. 8A to the orientation shown in FIG. 8B, the sensor 70, which is located at a fixed position within the handpiece 2 will be disposed adjacent to a different portion of the magnetically permeable member 60 associated with the outer cutting blade 10.

Figure 9A:
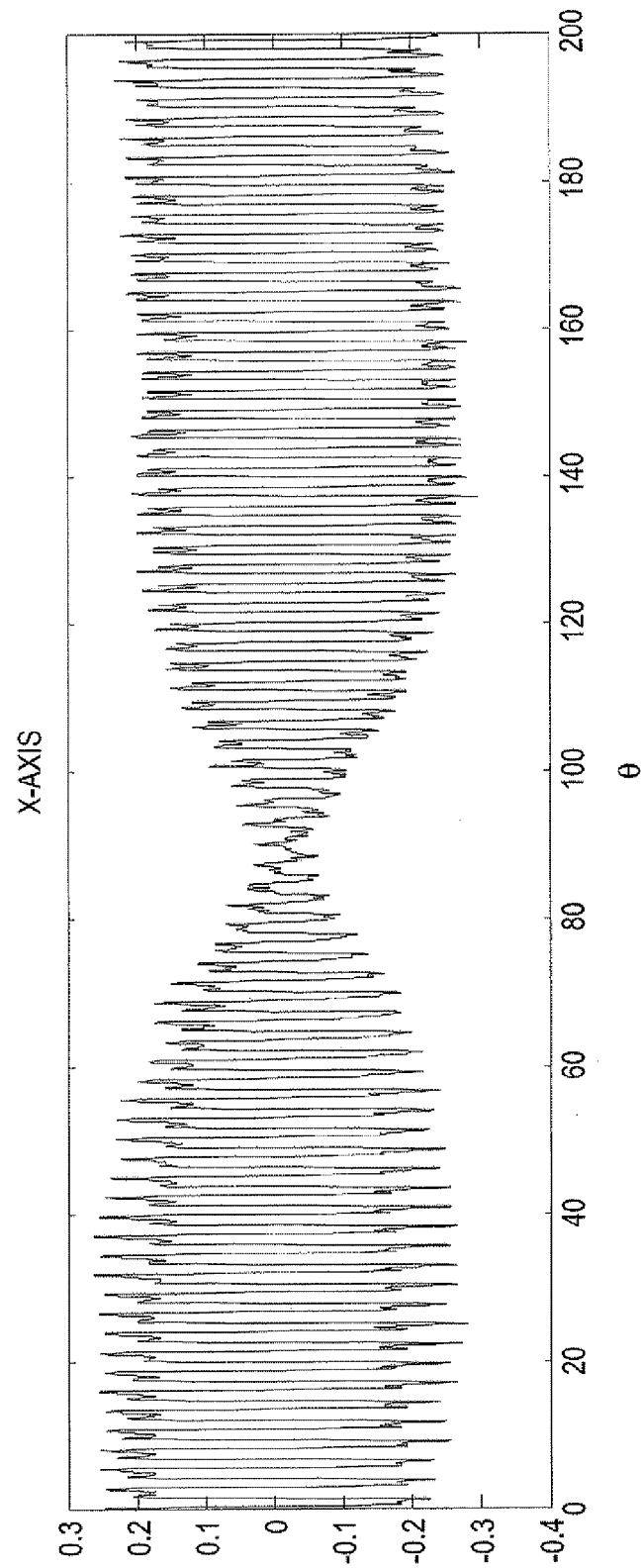
FIG. 9A shows the waveform of the X-axis component of the magnetic field sensed by the sensor for different positions of the sensor around the circumference of the outer cutting blade while the inner blade is spinning.
Figure 9B:
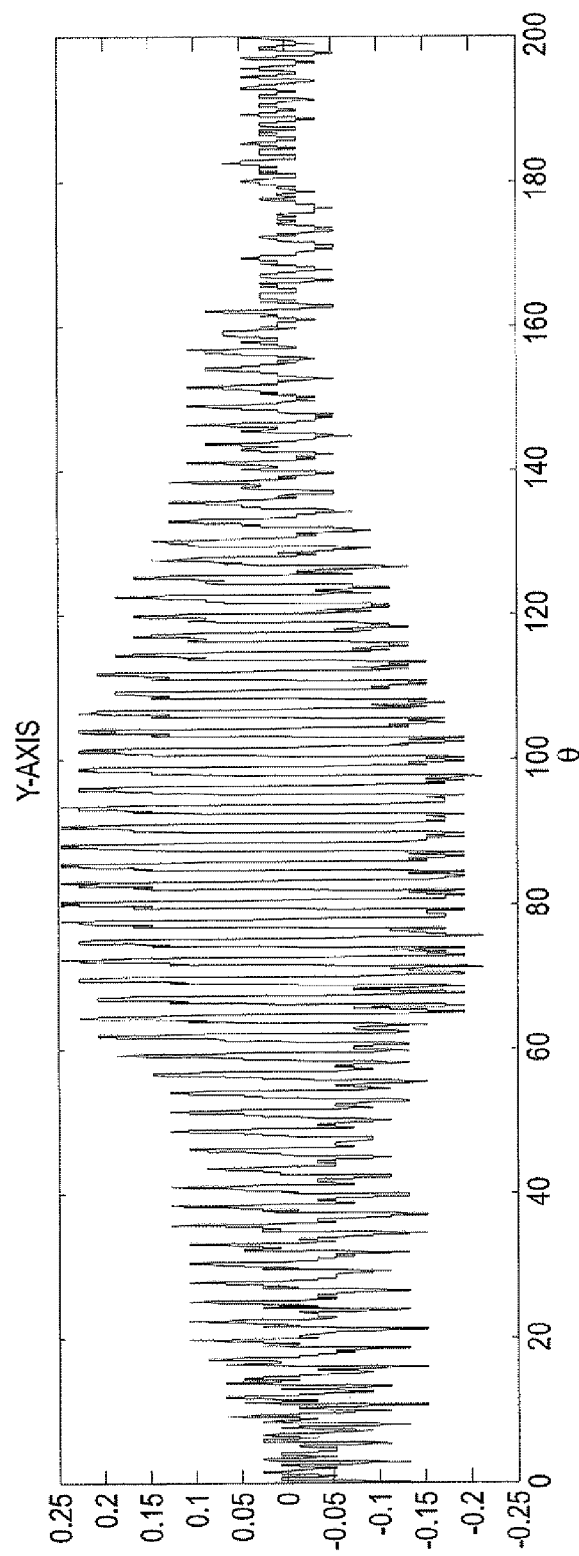
FIG. 9B is similar to FIG. 9A, but shows the waveform of the sensed Y-axis component of the magnetic field.

FIG. 9A shows the waveform of the magnetic field sensed by the sensor 70 in the X-axis direction for various locations of the sensor 70 relative to the magnetically permeable member 60. In particular, θ on the horizontal axis of FIG. 9A indicates the position of the sensor 70 relative to the magnetically permeable member 60 using the coordinate system shown in FIG. 7. Thus, at the origin, where θ=0, the sensor 70 would be on the axis $X^1$ shown in FIG. 7, whereas the sensor 70 would be positioned along the axis $Y^1$ of FIG. 7 (that is, the sensor 70 would be facing downward) for the value of θ=90° in FIG. 9A. As can be appreciated from FIG. 9A, the output of sensor 70 with respect to the magnetic flux detected in the X axis direction clearly shows oscillation in polarity regardless of the position of the sensor 70 relative to the magnetically permeable member 60. Accordingly, the output of sensor 70 can be used to indicate the position of the inner cutting blade 9 relative to the outer cutting blade 10 for any rotational orientation of the outer cutting blade 10 relative to the handpiece 2. FIG. 9B shows a waveform similar to FIG. 9A except that it shows the magnetic flux detected along the Y-axis direction of the sensor 70.

Figure 10A:
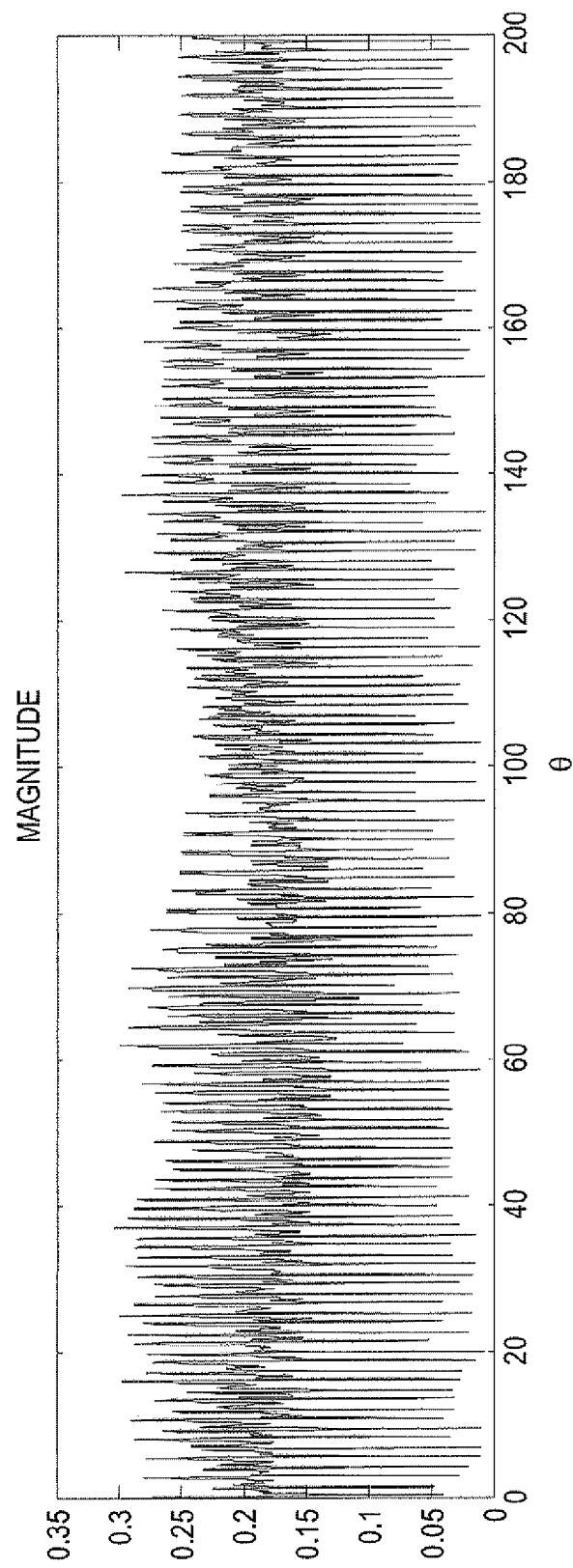
FIG. 10A shows the magnitude of the vectorized X- and Y-axis components of the magnetic field sensed by the sensor around the circumference of the outer cutting blade.
Figure 10B:
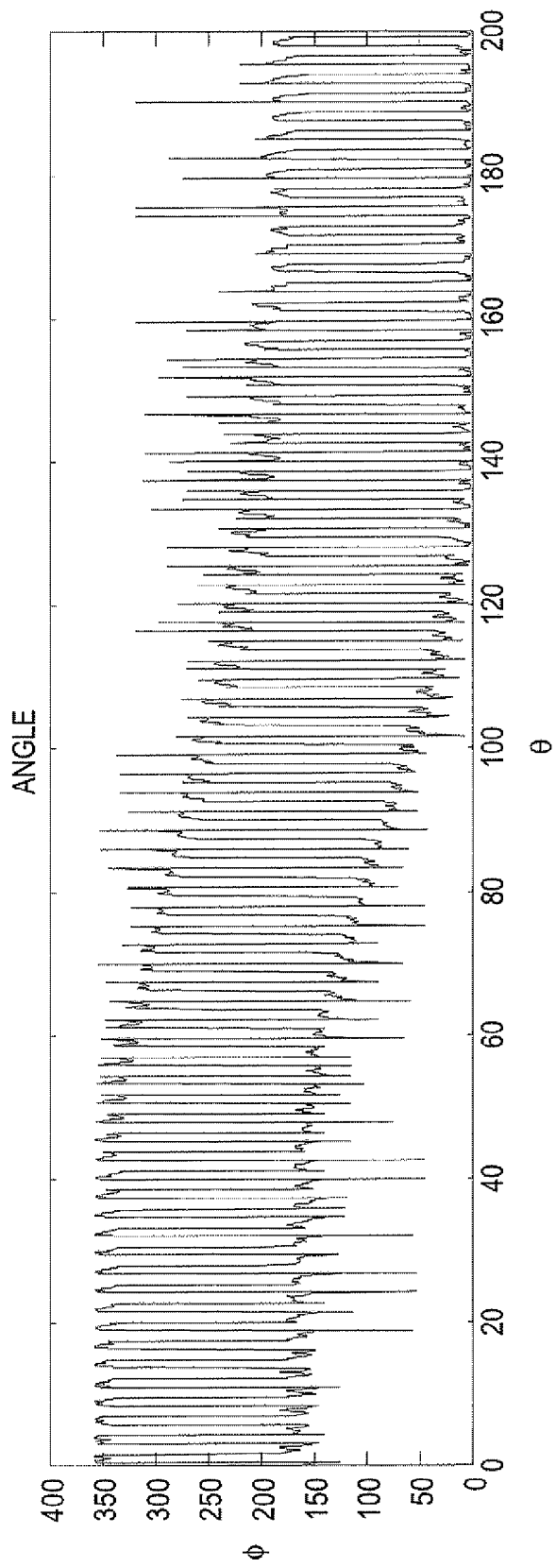
FIG. 10B is similar to FIG. 10A, but shows the angle of the vectorized X- and Y-axis components relative to a normal of the outer cutting blade.

The X and Y components of magnetic flux detected by the sensor 70 can be vectorized to give a better sense of where magnetic vectors are pointing. FIG. 10A shows the magnitude of the vectorized X and Y components for various positions of the sensor 70 around the circumference of the magnetically permeable material 60. FIG. 10B shows the angle φ of the magnetic vector for various positions of the sensor 70 around the circumference of the magnetically permeable material 60. The angle φ is relative to a natural of the magnetic circular surface of the magnetically permeable member 60.

Figure 11A:
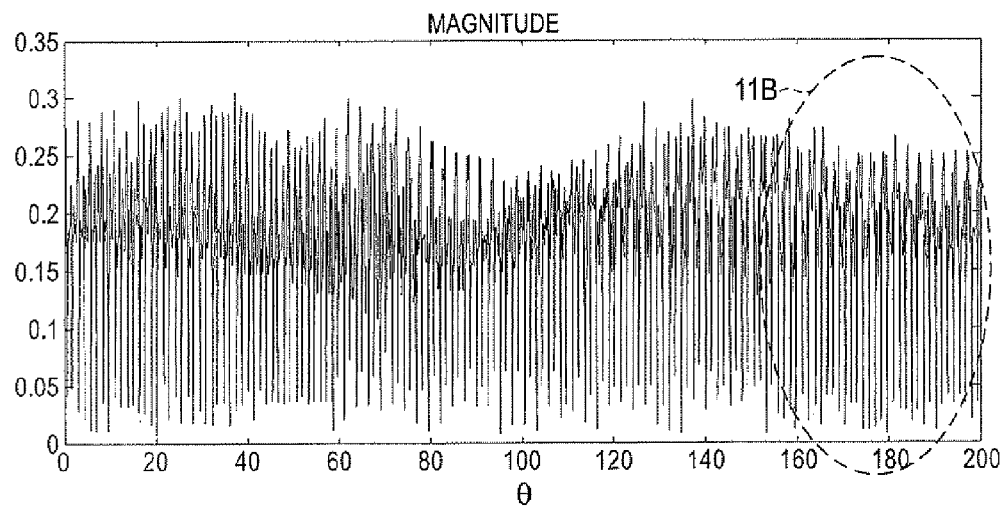
FIG. 11A is similar to FIG. 10A and indicates the portion thereof which is shown enlarged in FIG. 11B.
Figure 11B:
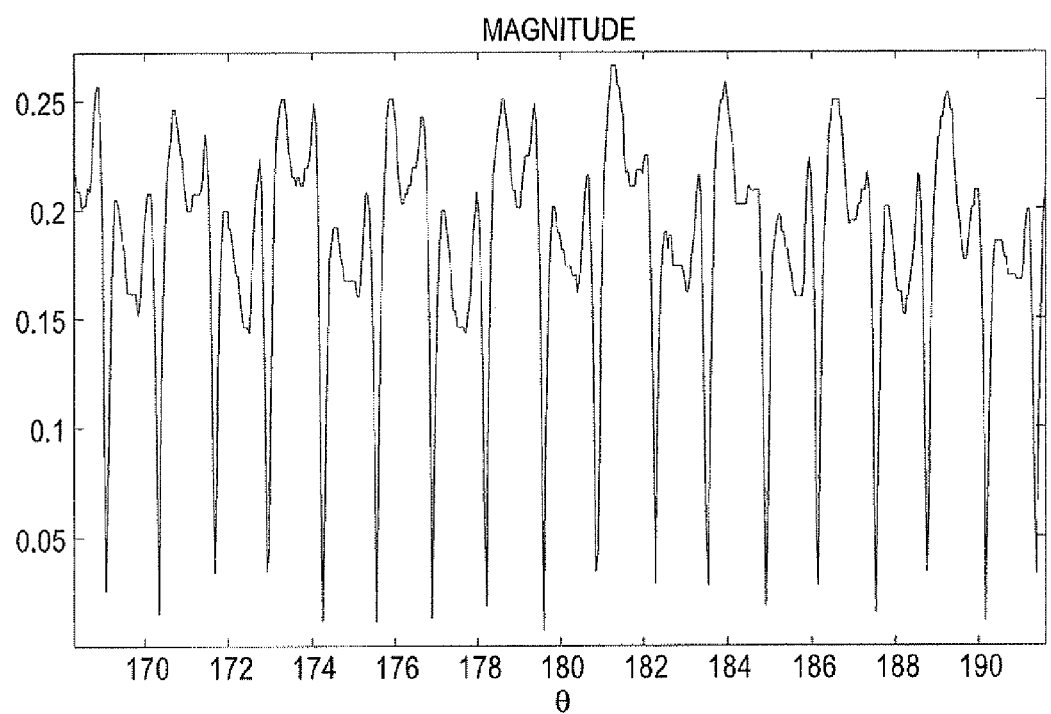
Figure 14:
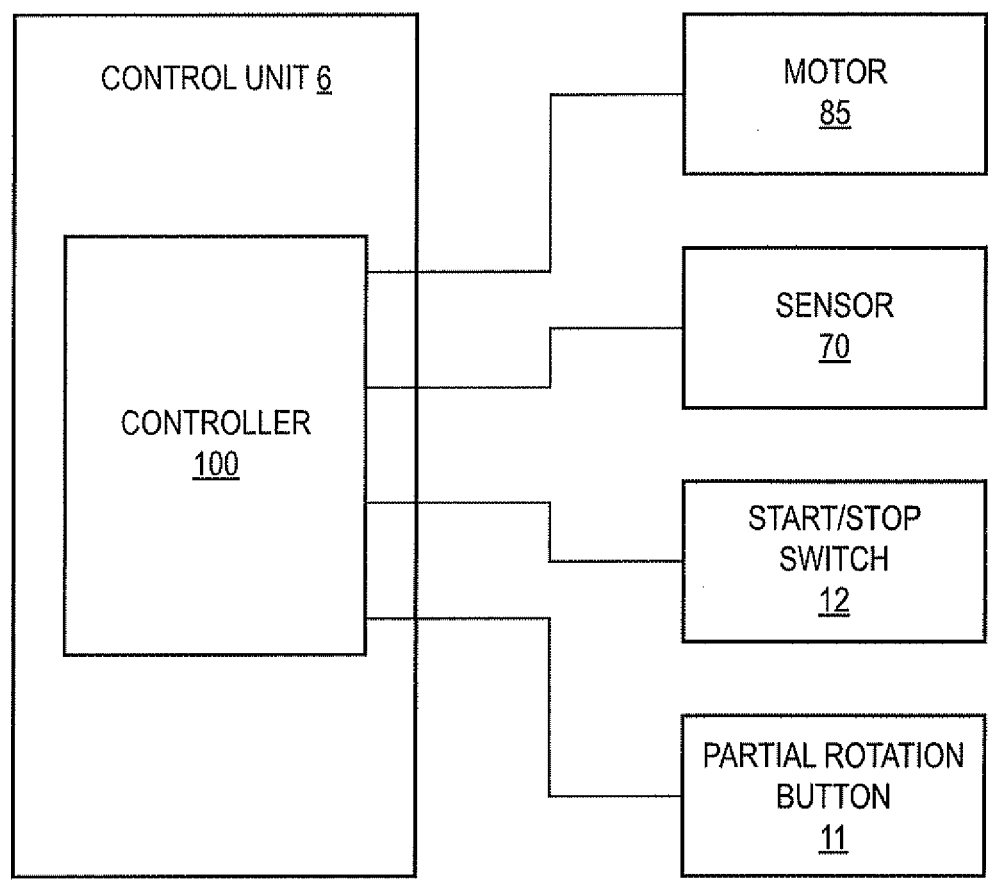
FIG. 14 is a block diagram of the control system that controls stopping rotation of the inner tube using the signal output by the sensor.

FIG. 11A is similar to FIG. 10A and indicates the portion thereof which is shown enlarged in FIG. 11B. Referring to FIG. 11B, each dip in the waveform represents magnets (50a and 50b) transitioning from under one of the magnetically permeable members 60a or 60b to the other magnetically permeable member 60b or 60a. As each of the magnets 50a, 50b moves under a specific permeable material piece 60a, 60b it does not induce uniform magnetic field across the whole material piece, and thus the magnitude of the waveform varies. However, the sharp drops in the waveform are easily identifiable by signal processing software implemented by the system controller 100 (FIG. 14), and thus the waveform can be used to detect the position of the inner cutting blade 9 relative to the outer cutting blade 10.

Figure 12A:
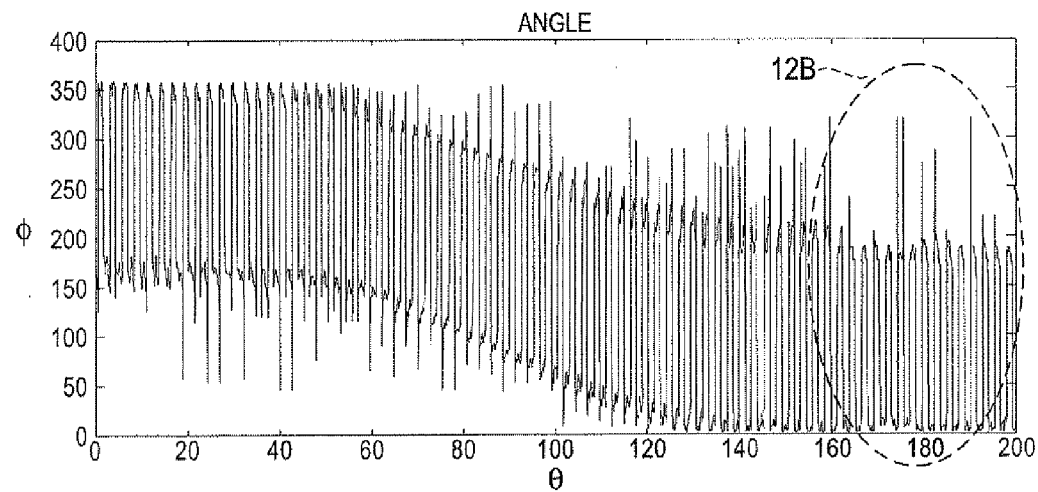
FIG. 12A is similar to FIG. 10B and indicates the portion thereof which is shown enlarged in FIG. 12B.
Figure 12B:
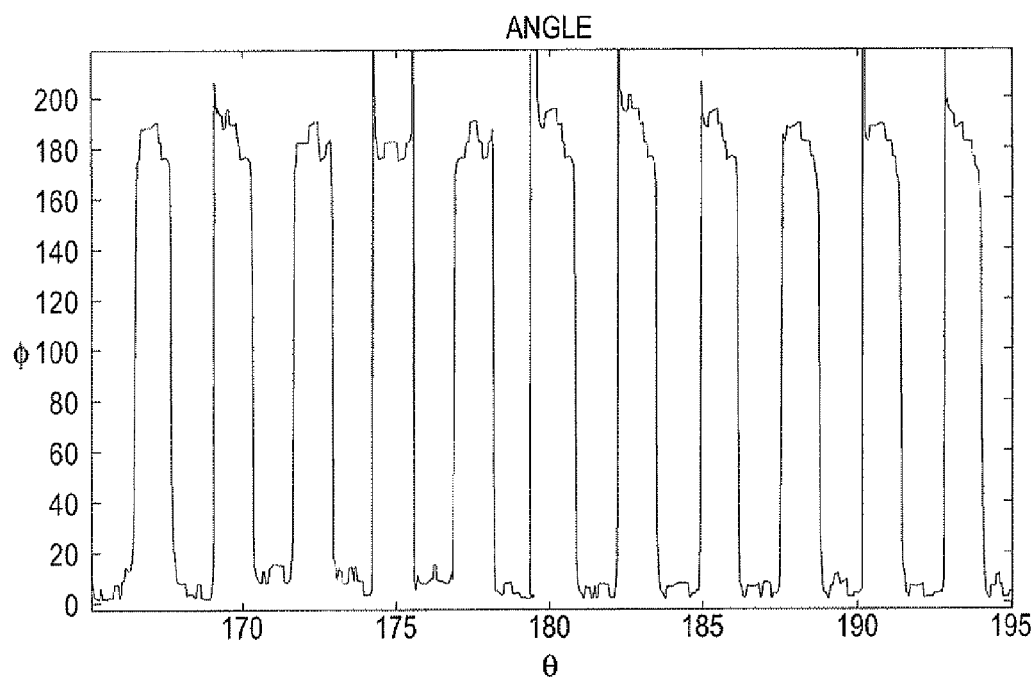

FIG. 12A is similar to FIG. 10B and indicates the portion thereof which is shown enlarged in FIG. 12B. FIG. 12B shows the angle φ of the detected magnetic flux. Each transition of φ from 0 to 180° represents magnets 50a, 50b transitioning from under one of the magnetically permeable pieces 60a to the other magnetically permeable piece 60b. As the magnets 50a, 50b move under a specific magnetically permeable material piece 60a, 60b, the vector orientation is fairly stable. Thus, the detected angle also can be used by controller 100 to determine the position of the inner cutting blade 9 relative to the outer cutting blade 10.

Figure 13A:
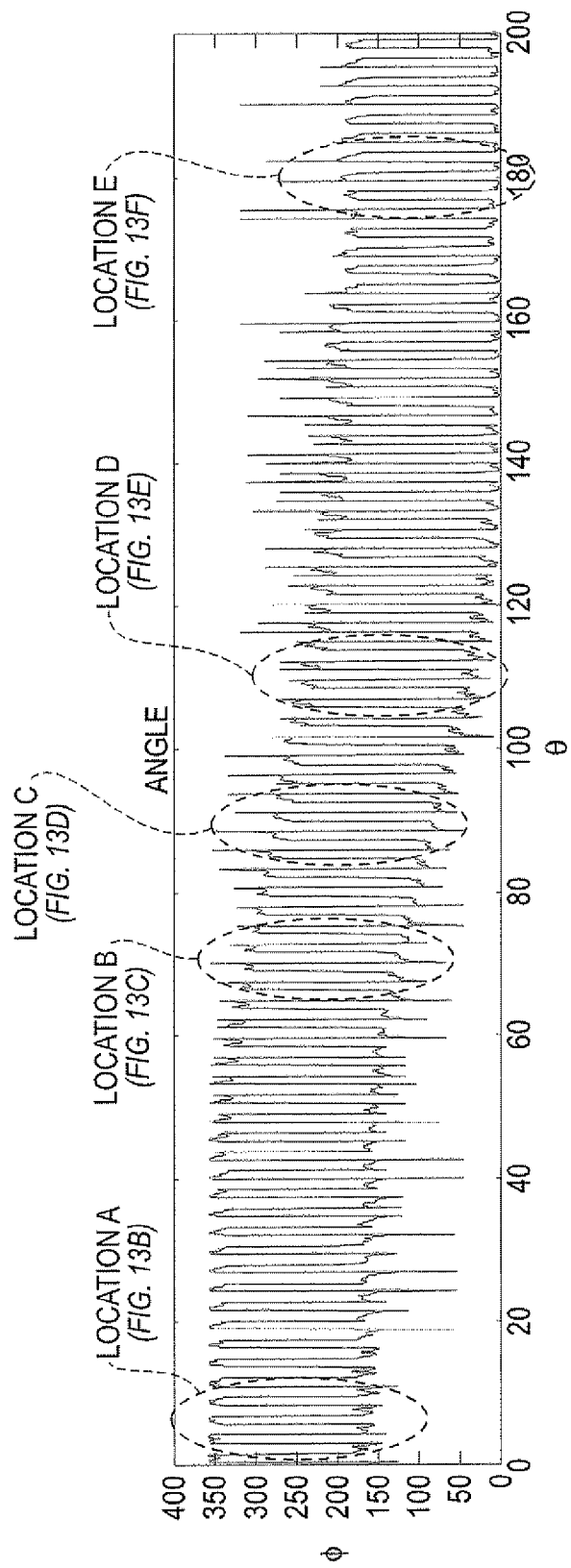
FIG. 13A shows the FIG. 10B waveform correlated to the position of the sensor relative to the magnetically permeable pieces at five different locations around the circumference of the outer cutting blade which are individually shown in FIGS. 13B-13F.
Figure 13B:
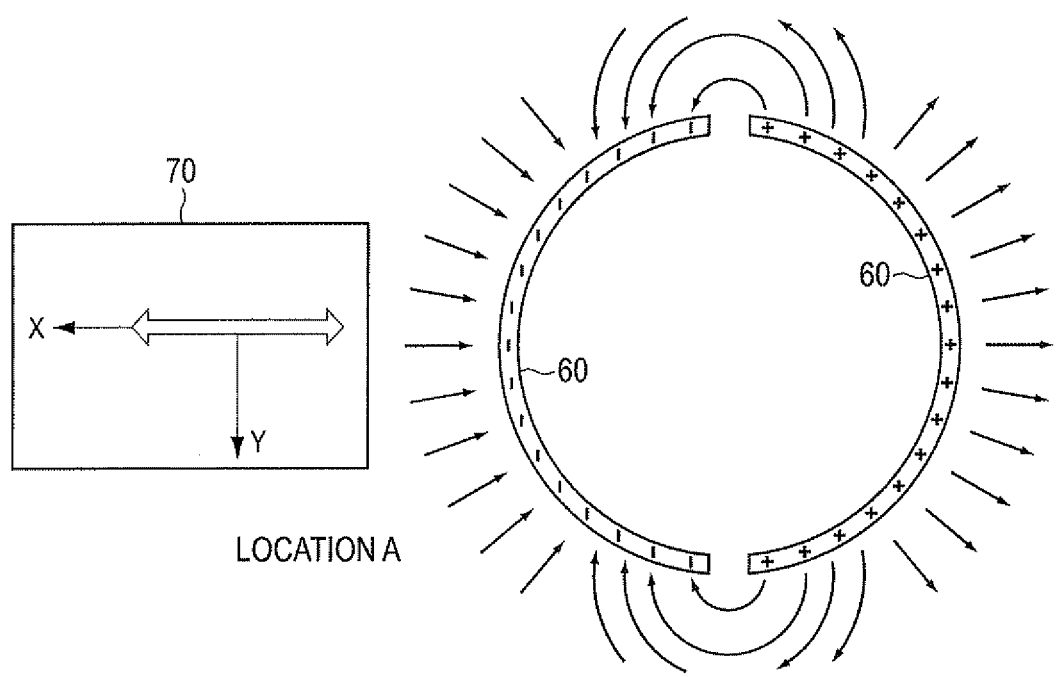
Figure 13C:
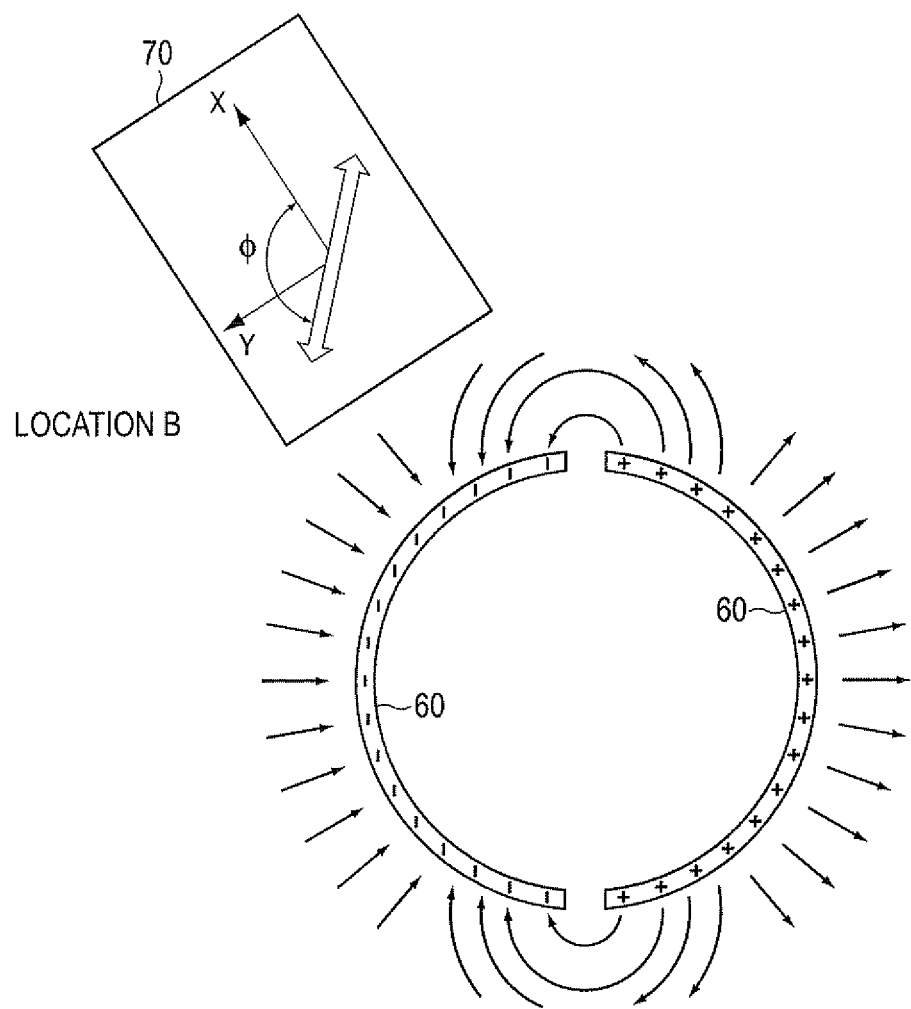
Figure 13D:
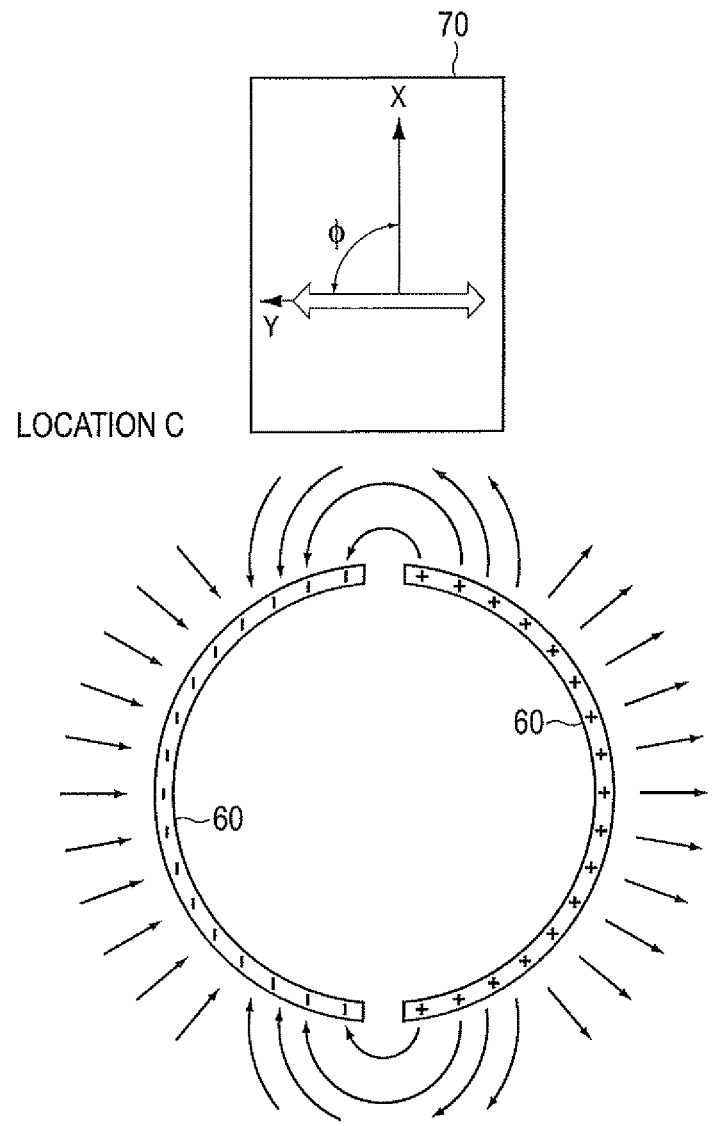
Figure 13E:
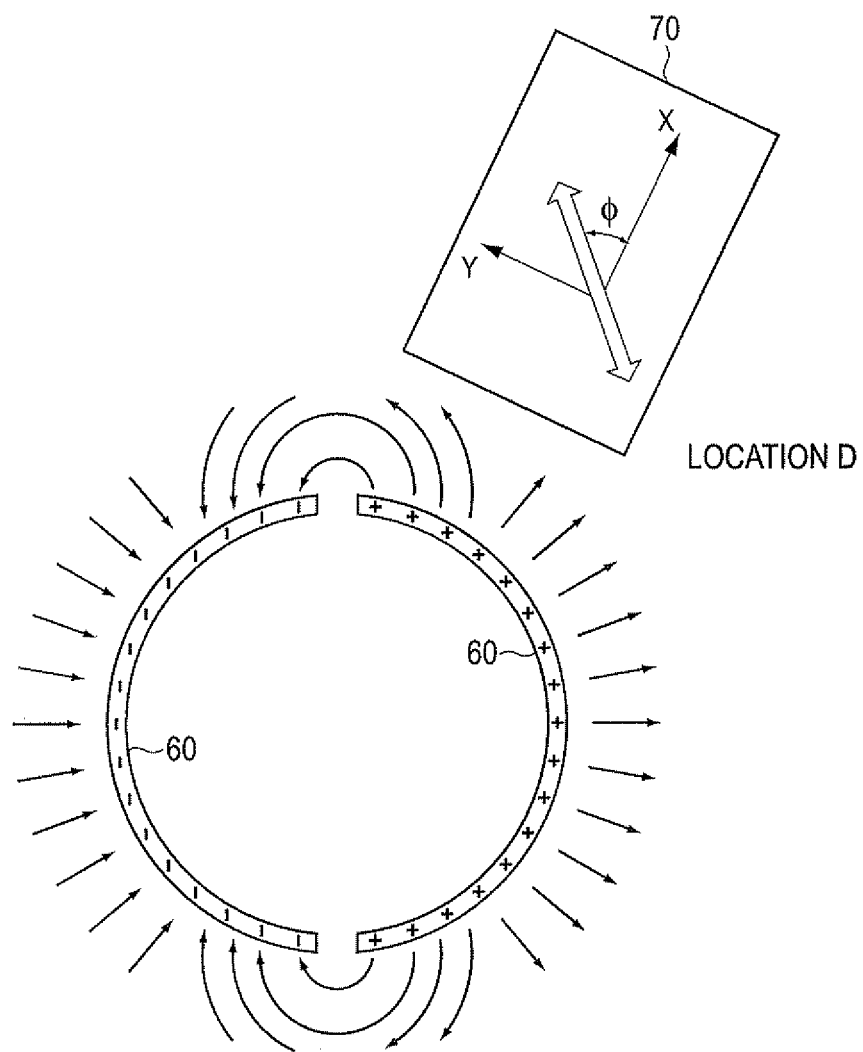
Figure 13F:
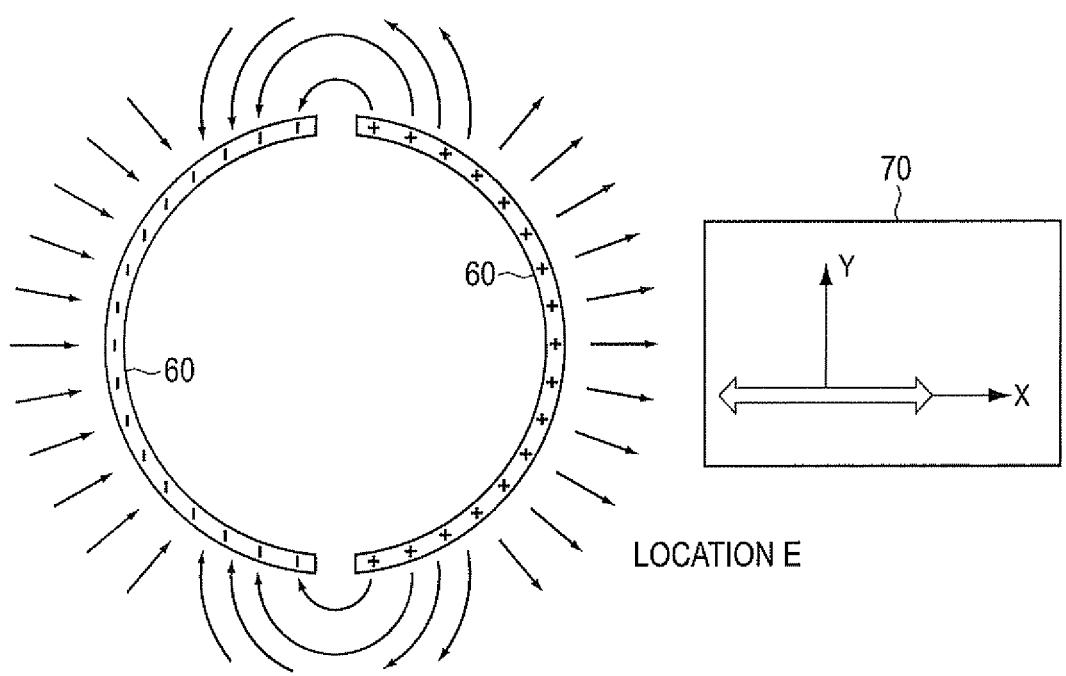

FIG. 13A shows the FIG. 10B waveform correlated to the position of the sensor at five different locations (labeled A, B, C, D and E) around the circumference of the magnetically permeable member 60. In particular, and as shown in FIG. 13B, location A corresponds to the waveform when the sensor 70 is located with its X-axis at 0° (using the coordinate system defined in FIG. 7), whereas location C (shown in FIG. 13D) and location E (shown in FIG. 13F) correspond to the waveform when the sensor 70 is located at 90° and 180°, respectively. Locations B and D (shown in FIGS. 13C and 13E, respectively) correspond to the waveform when the sensor 70 is located at approximately 70° and 110°, respectively. As demonstrated by location C (FIG. 13D), a useful waveform is output even when the sensor 70 is located adjacent to one of the gaps G between the two magnetically permeable pieces 60A and 60C.

Because the positional relationship between the magnets 50a and 50b and the cutting window 30 of the inner cutting blade 9 is fixed, and because the positional relationship between the magnetically permeable material pieces 60a and 60b and the cutting window 40 of the outer cutting blade 10 is fixed, the signal output by sensor 70 can be interpreted by signal processing software and/or hardware of the controller 100 to determine the position of the cutting windows 30 and 40 relative to each other. For example, referring to FIG. 3, if the cutting window 40 of outer cutting blade 10 faces out of the page, the magnetically permeable material pieces 60a and 60b could be arranged on the hub 15 so that the gaps G are on the top side and the bottom side in FIG. 3 of the hub 15. Similarly, if the cutting window 30 of the inner cutting blade 9 faces out of the page as shown in FIG. 3, the magnets 50a and 50b could be arranged so that they extend from the upper side and the lower side of the hub 13 in FIG. 3. Accordingly, each time the magnets 50a and 50b are aligned with the gaps G, the windows 30 and 40 either will be completely aligned as shown in FIG. 3 and FIG. 4, or completely misaligned as shown in FIG. 5.

According to one embodiment, when a surgeon issues a rotation stop command by releasing the foot switch 12, the controller 100 uses the information derived from the output of sensor 70 to control the motor 85 that rotates the inner cutting blade 9 to stop rotation of the inner cutting blade 9 so that the magnets 50a and 50b are located adjacent to the gaps G (that is, located at a predetermined stop position). This can be done by initially slowing the rotation speed of the inner cutting blade 9 upon issuance of the stop command, and then monitoring the output of sensor 70 until its output indicates alignment of the magnets 50a and 50b with the gaps, at which time the inner cutting blade 9 is stopped. Alternatively, upon receipt of the stop command, the controller 100 could allow the inner cutting blade 9 to stop at any random position. Then, upon receipt of a command (for example, caused by depression of a partial rotation button 11 described below) the controller could cause the motor to slowly rotate the inner cutting blade 9 while monitoring the output of the sensor 70 until the sensor output indicates that the magnets 50a and 50b are aligned with the gaps G (that is, located at a predetermined stop position). In either of the above instances, once the inner cutting blade 9 is stopped at the predetermined stop position, a surgeon viewing the cutting tip 8a could then determine whether the cutting windows are completely aligned or completely misaligned, and then press the partial rotation button 11 (for example, on the handpiece 2) to cause the inner cutting blade 9 to rotate by 180° if necessary to place the cutting blades in the desired orientation. For example, if the final stopping point of the inner cutting blade 9 is what the surgeon desires (either completely aligned cutting windows or completely misaligned cutting windows), the surgeon would need to take no further action. If, however, the position of the cutting blades is the opposite of what is desired (for example, if the inner cutting blade stopped with the windows completely aligned but the surgeon wants the windows to be completely misaligned), the surgeon could press the partial rotation button 11 to cause the inner cutting blade to rotate by 180°.

It also is possible to use the sensor 70 and hardware of the motor to enable the inner cutting blade 9 to be stopped at a position where it is half way between the position where the windows are completely aligned and the position where the windows are completely misaligned. In particular, the Hall sensor of the motor (hereafter referred to as the "motor Hall sensor") can be used to rotate the inner cutting blade by 90° from either of the positions where the windows are completely aligned or completely misaligned. In such an embodiment, one could transition through states: fully open (windows aligned), partially open (windows partially aligned), fully closed (windows completely misaligned), partially open (windows partially aligned), and back to fully open. This can be implemented by switching between rotation that use the outputs of sensor 70 and of the motor Hall sensor. One example is now provided. This logic/sequence would restart after any use of start/stop button for cutting purposes. One first press of the partial rotation button 11 (also called "toggle button") would be used to find the first magnet transition based on the output of sensor 70. Let's say that puts the blades at window fully open (aligned) position. Subsequent press of the toggle button would use the motor's Hall sensor and rotate the inner blade 9 by 90° (this would result in window partially open position). The following press of the toggle button would rotate the inner blade 9 until sensor 70 finds the next magnet transition, which would be an additional 90° rotation that would place the blades at the window fully closed position. The next toggle button press would use motor's Hall sensor again to progress by 90°, and so on. The motor's Hall sensor could not always be used to progress by 90° because the user can manually rotate outer blade at some point, and then the 90° increments would not key of the "home" position ("home" position being the window open or closed position).

Furthermore, it is possible to vary the geometry of the magnetically permeable material pieces 60a and 60b so that the controller 100 can automatically determine whether the cutting window 30 of the inner cutting blade 9 has stopped at a position that is completely aligned with or completely misaligned with the cutting window 40 of the outer cutting blade 10. For example, the edges of the pieces 60a and 60b could be varied (for example, using an intentional notch or discontinuity or using an angled slot), or the sizes of the two gaps G could be different from each other, such that the signal output by sensor 70 differs depending on which of the magnetic members 50a or 50b is located adjacent to which of the gaps G. One option for differentiating between the transitions of the magnetic members over the gaps is to eliminate one of the transitions, more specifically smooth one of the transitions out by having a diagonal gap, for example. Since we always rotate in one direction during homing, window open versus closed can be determined by whether sharp transition is leading or lagging in the square wave. Another option, is to not space the magnets 180° apart. For example, the magnets could be spaced by 120° and the same could be done with the permeable material, i.e. one spanning 120° and the other spanning 240°. This will eliminate one transition and will make the waveform non symmetric. The remaining sharp transition will indicate either window open or closed (depending on the blade construction). If, for example we choose the remaining sharp transition to correspond to the window open position, then the window closed can be obtained by progressing inner blade by another 180° by using the motor's Hall sensor.

In the illustrated embodiment, the inner and outer cutting blades 9 and 10 are straight. However, the surgical instrument 8 can have one or more bends in it such that it is not straight. In such an arrangement, the inner cutting blade 9 would be flexible. Flexible hollow cutting blades are known and used with curved cutting instruments. See, for example, U.S. Pat. No. 4,646,738, the disclosure of which is incorporated herein by reference in its entirety, and see, for example, U.S. Pat. No. 5,707,350, the disclosure of which is incorporated herein by reference in its entirety.

The illustrated exemplary embodiments of the surgical tool as set forth above are intended to be illustrative and not limiting. Various changes may be made without departing from the spirit and scope of the invention.

What is claimed is:

1. A surgical instrument comprising:
   an outer tube having a distal end, a proximal end and a cutting window near the distal end;
   an inner rotating member having a distal end, a proximal end and a cutting member near the distal end, the inner rotating member is rotatably disposed within the outer tube;
   a handpiece that is coupled to the inner rotating member and the outer tube near the proximal ends of the inner rotating member and the outer tube, the handpiece having a longitudinal axis; and
   a rotation sensor system including:
      a magnetic member provided on the inner rotating member near the proximal end of the inner rotating member;
      a magnetically permeable member provided on the outer tube near the proximal end of the outer tube; and
      a sensor provided on the handpiece and sensing magnetic flux of the magnetically permeable member adjacent to the sensor,
      wherein the magnetic member, the magnetically permeable member and the sensor are radially aligned with each other with respect to the longitudinal axis, with the magnetic member being disposed radially inward of the magnetically permeable member, and the magnetically permeable member being disposed radially inward of the sensor.

2. The surgical instrument of claim 1, wherein:
   the magnetic member includes two oppositely polarized magnets disposed at diametrically opposite positions relative to a longitudinal axis of the inner rotating member such that a polarity of an outwardly-facing pole of a first one of the magnets is opposite to a polarity of an outwardly-facing pole of a second one of the magnets.

3. The surgical instrument of claim 1, wherein:
   the magnetically permeable member includes two semicircular pieces of ferromagnetic material located on opposite circumferential segments near the proximal end of the outer tube, opposing ends of the two semicircular pieces of ferromagnetic material being separated from each other by gaps.

4. The surgical instrument of claim 1, wherein:
   the sensor is a dual axis linear magnetic sensor that senses magnetic flux in two perpendicular directions.

5. The surgical instrument of claim 1, wherein:
   the magnetic member includes two oppositely polarized magnets disposed at diametrically opposite positions relative to a longitudinal axis of the inner rotating member such that a polarity of an outwardly-facing pole of a first one of the magnets is opposite to a polarity of an outwardly-facing pole of a second one of the magnets;
   the magnetically permeable member includes two semicircular pieces of ferromagnetic material located on opposite circumferential segments near the proximal end of the outer tube, opposing ends of the two semicircular pieces of ferromagnetic material being separated from each other by gaps; and
   the sensor is a dual axis linear magnetic sensor that senses magnetic flux in two perpendicular directions.

6. The surgical instrument of claim 5, wherein the sensor outputs a sensor signal, the surgical instrument further comprising:
   a controller that determines a position of the cutting member relative to the cutting window based on the sensor signal.

7. The surgical instrument of claim 6, wherein, upon receipt of a stop command from a user of the surgical instrument, the controller stops rotation of the inner rotating member and positions the cutting member of the inner rotating member at a predetermined stop position relative to the cutting window of the outer tube.

8. The surgical instrument of claim 7, further comprising a coupling between the handpiece and the proximal end of the outer tube, the coupling including a first part on the handpiece and a second part on the proximal end of the outer tube, the first and second parts being adjustably attachable to each other at different selectable rotational orientations relative to the longitudinal axis of the handpiece so that a rotational orientation of the outer tube cutting window relative to the handpiece can be adjusted.

9. The surgical instrument of claim 1, wherein the sensor outputs a sensor signal, the surgical instrument further comprising:
   a controller that determines a position of the cutting member relative to the cutting window based on the sensor signal.

10. The surgical instrument of claim 9, wherein, upon receipt of a stop command from a user of the surgical instrument, the controller stops rotation of the inner rotating member and positions the cutting member of the inner rotating member at a predetermined stop position relative to the cutting window of the outer tube.

11. The surgical instrument of claim 10, wherein the predetermined stop position is one of the following two positions: (i) the cutting window of the outer tube is completely obstructed by the inner rotating member, and (ii) the cutting window of the outer tube is not obstructed by the inner rotating member.

12. The surgical instrument of claim 1, further comprising a coupling between the handpiece and the proximal end of the outer tube, the coupling including a first part on the handpiece and a second part on the proximal end of the outer tube, the first and second parts being adjustably attachable to each other at different selectable rotational orientations relative to the longitudinal axis of the handpiece so that a rotational orientation of the outer tube cutting window relative to the handpiece can be adjusted.

13. The surgical instrument of claim 1, wherein the inner rotating member is an inner tube and the cutting member is a cutting window near the distal end of the inner tube.

14. The surgical instrument of claim 1, further comprising a motor coupled to the inner rotating member to rotate the inner rotating member during a cutting operation.

\* \* \* \* \*